United States Patent [19]
Chiang et al.

[11] Patent Number: 5,177,248
[45] Date of Patent: Jan. 5, 1993

[54] PROCESS OF FORMING POLYSUBSTITUTED FULLERENES

[75] Inventors: Long Y. Chiang, Somerset; Ravindra B. Upasani, Flemington, both of N.J.; John W. Swirczewski, Kintnersville, Pa.

[73] Assignee: Exxon Research and Engineering Company, Florham Park, N.J.

[21] Appl. No.: 783,292

[22] Filed: Oct. 28, 1991

[51] Int. Cl.$^5$ .................................... C07C 69/753
[52] U.S. Cl. ................................. 560/86; 560/89; 564/308; 568/719
[58] Field of Search .............. 560/86, 89; 564/308; 568/719, 930

[56] References Cited

PUBLICATIONS

L. S. Sunderlin, et al.; Gas-Phase Reactivity of Fullerene Anions; 1991; 113, 5489–5490; J.A.C.S.
H. Selig, et al., Fluorinated Fullerenes, 1991, 113, 5475–5476, J. Am. Chem. Soc.
Christophe Jehoulet, et al., Electrochemical Reduction and Oxidation of $C_{60}$ Films, 1991, 113, 5456–5457, J. Am. Chem. Soc.
Joe M. Wood, et al., Oxygen and Methylene Adducts of $C_{60}$ and $C_{70}$, 1991, 113, 5907–5908, J. Am. Chem. Soc.
Joel M. Hawkins, et al., Organic Chemistry of $C_{60}$ (Buckminsterfullerene): Chromatography and Osmylation, 1990, 55, 6250–6252, J. Org. Chem.
Stephen G. Kukolich, et al., EPR Spectra of $C_{60}$ Anion and Cation Radicals, Aug. 2, 1991, vol. 182, No. 3.4, pp. 263–265, Chemical Physics Letters.
Paul J. Fagan, et al., The Chemical Nature of Buckminsterfullerene ($C_{60}$) and the Characterization of a Platinum Derivative, May 24, 1991, vol. 252, pp. 1160–1161, Science.
George A. Olah, et al., Chlorination and Bromination of Fullerenes. Nucleophilic Methoxylation of Polychlorofullerenes and Their Aluminum Trichloride Catalyzed Friedel-Crafts Reaction with Aromatics to Polyarylfullerenes, 1991, 113, 9384–9387, J. Am. Chem. Soc.
George A. Olah, et al., Polyarenefullerenes, $C_{60}(H-Ar)_n$ Obtained by Acid-Catalyzed Fullerenation of Aromatics, 1991, 113, 9387–9388, J. Am. Chem. Soc.

*Primary Examiner*—Marianne M. Cintins
*Assistant Examiner*—Michael B. Hydorn
*Attorney, Agent, or Firm*—Estelle C. Bakun

[57] ABSTRACT

The present invention is directed toward the preparation of novel polysubstituted fullerenes. The method of forming polysubstituted fullerenes comprises contacting a fullerene with an electrophilic reagent selected from the group consisting of nitronium ion and organic peracid, provided that when the electrophilic reagent is nitronium ion, the fullerene is subsequently contacted with a nucleophilic reagent.

4 Claims, No Drawings

PROCESS OF FORMING POLYSUBSTITUTED FULLERENES

FIELD OF THE INVENTION

The present invention is directed to polysubstituted fullerenes and the process of preparing such.

BACKGROUND OF DISCLOSURE

Fullerenes are hollow molecules composed of pure carbon atoms. Typically, fullerenes each have 12 pentagons, but differing numbers of hexagons. The pentagons are required in order to allow curvature and eventual closure of the closed surface upon itself. The most abundant species to date is the $C_{60}$ molecule or Buckminster Fullerene. $C_{60}$ consists of 12 pentagons and 20 hexagons and is classified as an icosahedron, the highest symmetry structure possible. The second most abundant species, $C_{70}$, contains 12 pentagons and 25 hexagons. To date, fullerenes containing up to 400 carbon atoms have been identified. Characteristic of fullerenes is their general formula $C_{2n}$ where n is greater than or equal to 25.

Fullerenes are produced by high temperature vaporization of solid graphite rods by resistive heating or arc heating in the presence of a few to several torr of rare gas. The soot produced by the vaporization contains varying levels of fullerenes, depending on the vaporization conditions. However, the majority of the fullerenes produced are $C_{60}$ and $C_{70}$, with $C_{60}$ being more abundant.

The fullerenes are extracted from the soot by placing the soot into a solvent in which the fullerenes are soluble. The solution is then filtered and allowed to evaporate to yield fullerene powders. Alternatively, the fullerenes can be purchased commercially.

SUMMARY OF THE INVENTION

One embodiment of the present invention is directed to polysubstituted fullerene moieties having a plurality of substituents thereon, selected from the group consisting of hydroxy, oxide, nitro, amino, organocarboxy, amide, and/or mixtures thereof.

Another embodiment is directed toward the preparation of the novel polysubstituted fullerenes. The method of forming polysubstituted fullerenes comprises contacting fullerenes with an electrophilic reagent such as nitronium ion or an organic peracid. When the electrophilic agent is nitronium ion, the fullerene is further contacted with a nucleophilic reagent. Polysubstituted fullerenes comprise a fullerene moiety selected from fullerenes or mixtures thereof having a plurality of substituents thereon.

The polysubstituted fullerenes are particularly useful as cross-linking agents in polymers and/or as core building blocks of star polymers. Indeed, the polysubstituted fullerene molecules, with hydroxy or amino groups as the major components of substitutions, provide a unique three-dimensional multi-functional precursor suitable for utilization as polymer cross-linking agents and core building blocks of star polymers. Fully converted fullerenes, such as polyhydroxylated fullerenes, poly(amino) fullerenes, and poly(aminohydroxy) fullerenes, give a maximum number, about 10 to 15, of polymer arms on the fullerene molecules. Partially substituted fullerenes, such as poly(amino-hydroxyacetoxy) fullerenes, poly(aminohydroxytrifluoroacetoxy) fullerenes, poly(nitrohydroxy) fullerenes, and poly(aminoacetamino) fullerenes, can be used to produce a lesser number of polymer arms, about 3-10, on the fullerene molecule.

DETAILED DESCRIPTION OF THE INVENTION

The present invention employs either nitronium ion or organic peracid induced electrophilic substitutions on a fullerene molecule, followed by a sequence of chemical transformation to introduce hydroxy, nitro, organocarboxy, amide, oxide, and amino groups onto the fullerene. Contact with the electrophilic reagent requires from about 10 to about 30 hours.

One embodiment of the present invention is directed to fullerenes having a variety of substituents thereon. The fullerenes are referred to, according to the substituents, as follows: polyhydroxylated fullerenes are fullerenes having hydroxy (OH) groups thereon, fullerene oxides are fullerenes having an oxygen group thereon, fullerenes having a mixture of hydroxy and oxygen groups thereon are referred to as $\alpha$-hydroxy hemiacetals, fullerenes having nitro ($NO_2$) groups thereon are polynitro fullerenes, fullerenes having both hydroxy and nitro groups thereon are poly(nitrohydroxy) fullerenes, fullerenes having both an organocarboxy ($RCO_2$) and OH group thereon are poly(hydroxyorganocarboxy) fullerenes, fullerenes having nitro, hydroxy, and acetoxy ($CH_3CO_2$) groups from acetic acid being used as the nucleophile are referred to as poly(nitrohydroxyacetoxy) fullerenes, when the nitro group of poly(nitrohydroxyacetoxy) fullerenes is hydrogenated to an amino ($NH_2$) group, the fullerene is referred to as poly(aminohydroxyacetoxy) fullerene, fullerenes having hydroxy and amino groups thereon are poly(aminohydroxy) fullerenes, fullerenes having nitro, hydroxy, and $CF_3CO_2$ groups thereon are poly(aminohydroxytrifluoroacetoxy) fullerenes, fullerenes having nitro and $CH_3CONH$ groups thereon are poly(nitroacetamino) fullerenes; fullerenes having amino and $CH_3CONH$ groups thereon are poly(aminoacetamino) fullerenes, fullerenes having only $NH_2$ groups thereon are polyamino fullerenes, fullerenes having nitro, hydroxy, and organocarboxy $RCO_2$ groups thereon are poly(nitrohydroxyorganocarboxy) fullerenes, and fullerenes having a nitro and an organocarboxy group thereon are poly(nitroorganocarboxy) fullerenes. These names are not limiting; fullerenes having other groups thereon resulting from the selection of a particular nucleophile in accordance with the invention would be similarly named.

The reaction of fullerenes, preferably $C_{60}$ and $C_{70}$ fullerenes and mixtures thereof, is carried out either in an aqueous medium in the presence of sulfuric acid and nitronium ion or in a non-aqueous medium with nitronium ion or organic peracid and various organic nucleophiles. The completion of reaction is easily determined by the reaction mixture turning clear brown or yellow.

In the aqueous chemistry, several different mixtures of acidic medium can be employed to prepare polyhydroxylated fullerenes. Acidic mixtures include concentrated sulfuric acid with concentrated nitric acid, triflic acid (trifluoromethanesulfonic acid) with potassium nitrate, concentrated sulfuric acid with potassium nitrate, fuming sulfuric acid (oleum) with concentrated nitric acid, and fuming sulfuric acid with nitronium tetrafluoroborate. The first four acid mixtures generate nitronium ion, the electrophilic reagent, in-situ and therefore must be run at a reaction temperature of between about 90°–115° C. to activate the dehydrative conversion of nitric acid to nitronium ion. The fifth method employs the direct use of nitronium ion and, hence, proceeds at a temperature of about 20°-50° C.

Once the reaction is complete, as evidenced by the formation of a clear brown solution, the reaction solution is diluted with water, followed by filtration, to remove unreacted fullerene particles. Neutralization with NaOH to precipitate product follows. The precipitation with NaOH can be achieved at a pH of aqueous solution higher than 9.0 and a low sulfate concentration (<2% by Wt.). A brown solid results, which is moderately soluble in water and very soluble in acidic water.

Removal of water from the partially hydrated product can be accomplished under vacuum at about 50° C., affording a product with a slightly lower solubility in water.

Upon completion of reaction, only trace amounts of starting $C_{60}$ and $C_{70}$ fullerenes are recovered. This is attributable to the fullerene intermediate, the partially substituted fullerene, having a higher solubility in acidic $H_2O$ than the $C_{60}$ and $C_{70}$ fullerenes themselves. Thus, the reaction tends to continue on the intermediate until completion. Analysis has shown that the ratio of hydroxy groups to fullerene molecule is about 5–32. Higher substitution is possible for fullerenes having greater than 70 carbon atoms.

The polyhydroxylated fullerenes often contain one to three sodium sulfate molecules per polyhydroxylated fullerene from the initial workup procedure using $H_2SO_4$. They can be further purified by redissolving them in dilute hydrochloric acid, followed by reprecipitation after neutralization with NaOH. Purification reduces the level of sodium sulfate to less than 0.3 molecules per fullerene. Complete removal of sodium sulfate can be accomplished by reverse phase chromatography.

In the present invention, when nitronium ion is the electrophilic reagent, it is probably the major active attacking species which reacts with the fullerene. When the present invention is carried out in the presence of sulfuric acid in aqueous solution, nitronium ion is formed by an acid-base reaction in which nitric acid acts as the base. The nitronium ion conversion is most effective above 90° C. Therefore, most reactions using sulfuric acid and nitric acid or potassium nitrate as reagents must be performed above that temperature. Alternatively, for the reaction to be carried out at a lower temperature of about 20°-50° C., nitronium tetrafluoroborate($NO_2 + BF_4-$) as a solid, or in tetramethylene sulfone can be used.

Probably, the electrophilic attack of nitronium ion on the olefin moiety of the fullerene is accomplished by the removal of a pair of electrons from the sextet in the benzene-like structure to give a carbocation as a resonance hybrid of arenium ions. Such carbocations are highly reactive. They can be reacted in the presence of nucleophilic reagents, such as water or organic acid, to afford a mixture of hydroxynitro or nitroalkylcarboxy fullerenes.

Probably, in the presence of strong acid such as sulfuric acid, the nitro functionality can be protonated and behave as an excellent leaving group that generates a new carbocation center adjacent to the hydroxy substitution. This carbocation intermediate can either react with water to give 1,2-diol product, rearrange with 1,4-shift and then react with water to afford 1,4-diol product, or form epoxide with the α-hydroxy group. The rearrangement of epoxide intermediate readily occurs to give fullerene oxide. Further reaction of fullerene oxide with nitronium ion and water in a similar mechanism, as discussed above, gives a product of α-hydroxy hemiacetal. Spectroscopic analysis shows that these α-hydroxy hemiacetal products are major components in the product mixture.

When nitronium ion is used as the electrophile in nonaqueous chemistry, the fullerene, preferably $C_{60}$, $C_{70}$, and mixtures thereof, is contacted with $NO_2BF_4$, either in solid form or in sulfolane solution, or another source of nitronium ion in the presence of a nucleophile. Suitable nucleophiles have the general formula

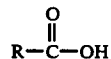

where R is a substituted or nonsubstituted alkyl or aryl group and wherein the substituent groups include OR', halides, —$NO_2$, —CN, and —NHCOR'. R' may be any aliphatic group. Examples of such nucleophiles include, but are not limited to, acetic acid and trifluoroacetic acid. When the carbocation intermediate, formed by reaction of the fullerene with nitronium ion, is allowed to react with water or acetonitrile as the nucleophile, a poly(nitrohydroxy) fullerene or poly(nitroacetamino) fullerene, respectively, can be obtained. The ratio of the nucleophilic substituent added to $C_{60}$ or $C_{70}$ is about 4 to about 15, though higher substitutions are possible for other fullerenes.

Catalytic hydrogenation of poly(nitrohydroxy) fullerenes, fullerenes having both $NO_2$ and OH groups thereon, converts the nitro group to the corresponding amino functionality. The reaction is carried out using palladium on carbon as a catalyst under a hydrogen pressure of about 50 psi for about 6 hours affording poly(aminohydroxy) fullerenes. Catalytic hydrogenation can be used to convert the $NO_2$ group on any polysubstituted fullerene to an amino group.

Polyhydroxylated or polyhydroxyorganocarboxy fullerenes can be prepared via the epoxidation method by reacting fullerenes, preferably $C_{60}$, $C_{70}$, and mixtures thereof, with organic peracids having the general formula

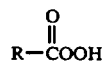

where R is a substituted or nonsubstituted alkyl group containing 1-20 carbon atoms or a substituted or nonsubstituted aryl group wherein the substituted groups include OH, halides, $NO_2$, and CN. For example, $C_{60}$, $C_{70}$ and mixtures thereof can be reacted with m-chloroperbenzoic acid in chloroform at 50°-90° C. to give a poly(hydroxyorganocarboxy). fullerene. The ratio of the organocarboxy substituent to $C_{60}$ or $C_{70}$ fullerene will be about 4 to about 10, though higher substitutions are possible for fullerenes containing greater than 70 carbon atoms. Hydrolysis, for example, with NaOH in methanol at about 50°-85° C. will yield polyhydroxylated fullerenes. Such polyhydroxylated fullerenes have IR spectrum closely resembling those of polyhydroxylated fullerenes obtained from the aqueous nitronium ion/acid reaction.

Polysubstituted fullerenes having at least three hydroxy or amino groups thereon and/or mixtures of such groups and oxide, nitro, organocarboxy, and amide substituent on the fullerene moiety can be used as cross-linking reagents in polymers. When used as such, about 0.2 to about 6% by weight of such cross-linking reagent to diacid chloride is required.

The polysubstituted fullerene is heated at about 50° C. to about 90° C. in the presence of a diacid chloride for about 10 to about 20 hours, followed by polymerization by adding a mixture of a diol and the same diacid chloride and continuing to heat for about 10 to about 20 hours. The diol selected contains about 4 to about 20 carbon atoms.

The following examples are intended to demonstrate the invention and are not limiting.

EXAMPLE 1

A reaction flask (50 ml) charged with a fullerene mixture of carbon 60 and carbon 70 (500 mg) in a ratio of 4:1 and distilled water (3.0 ml) was treated with concentrated sulfuric acid (15 ml) dropwise at 5° C. while vigorously stirring. A slow addition rate of acid is necessary to avoid a sharp increase in temperature. To this acid suspension, concentrated nitric acid (5.0 ml) was added dropwise at 5° C. The mixture was slowly heated to 115° C. and stirred at 115° C. for 4 hrs. The mixture was cooled to room temperature and added slowly into ice (50 g). The resulting aqueous acid solution was filtered through celite under vacuum to remove insoluble particles. The clear brown-orange filtrate was basified by an aqueous sodium hydroxide solution (2N) until the pH of the product solution reached 9.0 or higher. During the base neutralization, the color of solution slowly turned dark with a fine brown precipitate. The solution was allowed to stand at room temperature for 5 hrs to complete the precipitation. The precipitate was separated from solution by centrifugation. It was then washed and centrifuged three times with a dilute NaOH solution (1N), twice with methanol, and dried in vacuum at 50° C. to afford brown solids of polyhydroxylated fullerene (450 mg). IR (KBR)$v_{max}$ 3416 (s), 1598 (s), 1396 (s), and 1088 cm$^{-1}$. Mass spectrum of polyhydroxylated fullerene: m/e 758, 772, 790, 802, 814, 818, 832, 846, 860, 878, 894, 910, 926, 942, 956, 966, 1012, 1028, 1038, 1044, 1054, 1068, 1076, 1084, 1092, 1106, 1118, 1136, 1150, 1176, and 1188.

The combined aqueous solutions obtained from the above separation procedure were diluted with water to a total volume of 800 ml and allowed to stand at room temperature overnight to cause the further precipitation of fine brown solids. The solids were separated from solution and repeatedly washed with 1N NaOH (aq.) and methanol. After drying in vacuum at 50° C., a second crop of polyhydroxylated fullerenes (80 mg) was obtained as a brown solid.

EXAMPLE 2

A reaction flask (25 ml) charged with a fullerene mixture of carbon 60 and carbon 70 (200 mg) and distilled water (0.5 ml) was treated dropwise with triflic acid (trifluoromethanesulfonic acid, 5 ml) at 5° C. while vigorously stirring. A slow addition rate of acid is necessary to avoid a sharp increase of temperature. To this acid suspension potassium nitrate (1 g) was added portionwise at 5° C. The mixture was slowly heated to 110° C. and stirred at 110° C. for 4 hrs. The mixture was cooled to room temperature and added slowly into ice (20 g). The resulting aqueous acid solution was filtered through celite under vacuum to remove insoluble particles. The clear brown-orange filtrate was basified by an aqueous sodium hydroxide solution (2N) until the pH of the product solution reached 9.0 or higher. During the base neutralization, the color of solution slowly turned to dark with a fine brown precipitate. The solution was allowed to stand at room temperature for 5 hrs to complete the precipitation. The precipitate was separated from solution by centrifuge action. It was then washed and centrifuged three times with a dilute NaOH solution (1N), twice with methanol, and dried in vacuum at 50° C. to yield brown solids of polyhydroxylated fullerene (90 mg).

The insoluble solids remaining on the celite were extracted with toluene (100 ml) and filtered under vacuum. The toluene solution was dried on the rotary evaporator to remove all the solvent. The resulting dark brown solid (150 mg) was identified to be a mixture of carbon 60 and carbon 70 fullerenes.

EXAMPLE 3

A reaction flask (50 ml) charged with a fullerene mixture of carbon 60 and carbon 70 (500 mg) and distilled water (3.0 ml) was treated with concentrated sulfuric acid (15 ml) dropwise at 5° C. while vigorously stirring. A slow addition rate of acid is necessary to avoid a sharp increase in temperature. To this acid suspension potassium nitrate (3.5 g) was added dropwise at 5° C. The mixture was slowly heated to 90° C. and stirred at 90° C. for 24 hrs. It was cooled to room temperature and added slowly into ice (50 g). The resulting aqueous acid solution was filtered through celite under vacuum to remove insoluble particles. The clear brown-orange filtrate was basidified by an aqueous sodium hydroxide solution (2N) until the pH of the product solution reached 9.0 or higher. During the base neutralization, the color of solution slowly turns to dark with a fine brown precipitate. The solution was allowed to stand at room temperature for 5 hrs to complete the precipitation. The precipitation was separated from solution by centrifugation. It was then washed and centrifuged three times with a dilute NaOH solution (1N), twice with methanol, and dried in vacuum at 50° C. to afford brown solids of polyhydroxylated fullerene (550 mg).

The combined aqueous solution obtained from the above separation procedure was diluted with water to a total volume of 800 ml and allowed to stand at room temperature overnight to cause the further precipitation of fine brown solids. The solids were separated from solution and repeatedly washed with 1N NaOH (aq.) and methanol. After drying in vacuum at 50° C., a second crop of polyhydroxylated fullerene (150 mg) was obtained as a brown solid.

EXAMPLE 4

A reaction flask (50 ml) charged with a fullerene mixture of carbon 60 and carbon 70 (500 mg) and fuming sulfuric acid (oleum, 15 ml) was allowed to stir for 3 hrs to give a green suspension. The mixture was treated with distilled water (3.0 ml) dropwise at 5° C. while vigorously stirring. A slow addition rate of water is necessary to avoid a sharp increase in temperature. To this acid suspension concentrated nitric acid (5.0 ml) was added dropwise at 5° C. The mixture was slowly heated to 115° C. and stirred at 115° C. for 4 hrs. The mixture was cooled to room temperature and added slowly into ice (50 g). The resulting aqueous acid solution was filtered through celite under vacuum to remove insoluble particles. The clear brown-orange filtrate was basidified by an aqueous sodium hydroxide solution (2N) until the pH of the product solution reached 9.0 or higher. During the base neutralization, the color of solution slowly turns to dark brown with a fine brown precipitate. The solution was allowed to stand at room temperature for 5 hrs to complete the precipitation. The precipitate was separated from solution by centrifugation. It was then washed and centrifuged three times with a dilute NaOH solution (1N), twice with methanol, and dried in vacuum at 50° C. to afford brown solids of polyhydroxylated fullerene (610 mg).

The combined aqueous solutions obtained from the above separation procedure were diluted with water to a total volume of 800 ml and allowed to stand at room temperature overnight to cause the further precipitation of fine brown solids. The solids were separated from solution and repeatedly washed with 1N NaOH (aq.) and methanol. After drying in vacuum at 50° C., a second crop of polyhydroxylated fullerene (160 mg) was obtained as a brown solid.

EXAMPLE 5

A reaction flask (25 ml) charged with a fullerene mixture of carbon 60 and carbon 70 (200 mg) and fuming sulfuric acid (oleum, 8 ml) was allowed to stir for 2 hrs to give a green suspension. To this acid suspension water (2 ml) and nitronium tetrafluoroborate (480 mg) were added portionwise at ambient temperature. The mixture was heated to 50° C. and stirred at 50° C. for a period of 16 hrs. It was cooled to room temperature and added slowly into ice (30 g). The resulting aqueous acid solution was filtered through celite under vacuum to remove insoluble particles. The clear brown-orange filtrate was basidified by an aqueous sodium hydroxide solution (2N) until the pH of the product solution reached 9.0 or higher. During the base neutralization, the color of solution slowly turns to dark with a fine brown precipitate. The solution was allowed to stand at room temperature for 5 hrs. to complete the precipitation. The precipitate was separated from solution by centrifugation three times with a dilute NaOH solution (1N), twice with methanol, and dried in vacuum at 50° C. to afford brown solids of polyhydroxylated fullerene (320 mg).

EXAMPLE 6

A reaction flask (25 ml) charged with a fullerene mixture of carbon 60 and carbon 70 (70 mg) in methylene chloride (dried over molecular sieve) was treated with nitronium tetrafluoroborate (0.5 m in sulfolane solution), $NO_2BF_4$ (200 mg) and acetic acid (1.0 ml). The mixture was stirred at 23° C. for a period of 14 hrs. The resulting orange solution was neutralized with potassium carbonate (1.5 g) and filtered through celite. The filtrate was evaporated to dryness and the residue was stirred with ether for 5 min. The ether insoluble solid was collected by the centrifuge technique and dried under vacuum to afford yellow-brown solids of poly(nitrohydroxy acetoxy) fullerene (90 mg). Elemental analysis indicated that the composition of the compound is best fit with a unit formula $(C_{74}H_{24}N_{3.8}O_{25})$ of $C_{60}(CH_3CO_2)_7(NO_2)_{3.8}(OH)_{3.2}$. Found: C, 59.91; H, 2.14; N, 3.47; O, 28.18; S, 2.08 (from sulfolane residue). IR (KBr) $\upsilon_{max}$ 3439, 2940, 1816, 1753, 1829, 1567, 1372, 1337, 1220, 1080, 1052, and 807 cm$^{-1}$. $^1$H NMR (THF-$d_8$) $\delta$2.0–2.2 (bs, $CH_3$). $^{13}$C NMR (THF-$d_8$) $\delta$20 ($CH3$), 150, 170 (carbonyl). Mass spectrum of the compound using pure carbon 60 as a starting material: m/e 720, 737, 753, 769, 780, 787, 797, 813, 829, 840, 845, 857, 861, 873, 889, 901, 919, 933, 949, 965, 978, 990, 1009, 1023, 1035, 1052, 1058, 1065, 1069, 1081, 1085, 1099, 1105, 1114, 1128, 1153, 1231, 1289, 1306, 1347, 1362, and 1394.

To a thick-wall reactor (25 ml) connected with a hydrogen cylinder was charged the poly(nitrohydroxyacetoxy) fullerene (50 mg), palladium on carbon (Pd/C, 20 mg), and tetrahydrofuran (10 ml). The mixture was stirred and maintained under a hydrogen pressure of 50 psi for 6 hrs. At the end of reaction, the resulting suspension was filtered through celite to remove catalyst residues. The filtrate was then dried by solvent evaporation to give brown solids of poly(aminohydroxyacetoxy) fullerene (35 mg). IR (KBr) $\upsilon_{max}$ 3618 ($NH_2$), 3415 (w), 2948, 2863, 1637 (w), 1431, 1310, 1228, 1154, 1111, 868, 769, and 581 cm$^{-1}$.

To a reaction flask (25 ml) charged with the poly(aminohydroxyacetoxy) fullerene (50 mg) and methanol (10 ml) was added sodium hydroxide (150 mg). The mixture was heated at 60°–70° C. overnight with stirring. At the end of reaction, water (50 ml) and NaOH (200 mg) was added to cause the precipitation of poly(aminohydroxy) fullerene (40 mg).

EXAMPLE 7

A reaction flask (25 ml) charged with a fullerene mixture of carbon 60 and carbon 70 (70 mg) in methylene chloride (dried over molecular sieve) was treated with nitronium tetrafluoroborate (0.5 m in sulfolane solution), $NO_2BF_4$ (200 mg) and trifluoroacetic acid (1.0 ml). The mixture was stirred at 23° C. for a period of 14 hrs. Water was added to the resulting yellow-orange solution to cause the precipitation of solids. The solid was collected by the centrifuge technique, washed with water, and dried under vacuum to afford yellow-orange solids of poly(nitrohydroxytri-fluoroacetoxy) fullerene (93 mg). Elemental analysis indicated that the composition of the compound was: C, 57.17; H, 1.98; N, 2.41; O, 27.17; F, 9.21. IR (KBr) $\upsilon_{max}$, 3441, 1629, 1567, 1333, 1290, 1138, 1084, and 815 cm$^{-1}$.

To a thick-wall reactor (25 ml) connected with a hydrogen cylinder was charged the poly(nitrohydroxytrifluoroacetoxy) fullerene (50 mg), palladium on carbon (Pd/C, 20 mg), and tetrahydrofuran (10 ml). The mixture was stirred and maintained under a hydrogen pressure of 50 psi for 6 hrs. At the end of reaction, the resulting suspension was centrifuged to remove catalyst residues. The solution was then dried by solvent evaporation to give yellow-brown solids of poly(aminohydroxytrifluoroacetoxy) fullerene (27 mg).

To a reaction flask (25 ml) charged with the poly(aminohydroxytrifluoroacetoxy) fullerene (25 mg) and methanol (5 ml) was added sodium hydroxide (80 mg). The mixture was heated at 60°–70° C. for overnight with stirring. At the end of reaction, water (30 ml) and NaOH (100 mg) was added to cause the precipitation of poly(aminohydroxy) fullerene (40 mg).

EXAMPLE 8

A reaction flask (25 ml) charged with a fullerene mixture of carbon 60 and carbon 70 (50 mg) in methylene chloride (dried over molecular sieve) was treated with nitronium tetrafluoroborate (0.5 m in sulfolane solution), $NO_2BF_4$ (150 mg). The mixture was stirred at 23° C. for a period of 14 hrs. Water was added to the resulting solution to cause the precipitation of solids. The solid was collected by the centrifuge technique, washed with water, and dried under vacuum to afford brown solids of poly(nitrohydroxy) fullerene (63 mg). Elemental analysis indicated that the composition of the compound was: C, 60.76; H, 1.73; N, 3.06; O, 26.28. IR (KBr) $\upsilon_{max}$ 3450, 1656, 1567, 1337, 1092, and 815 cm$^{-1}$.

To a thick-wall reactor (25 ml) connected with a hydrogen cylinder was charged the poly(nitrohydroxy) fullerene (40 mg), palladium on carbon (Pd/C, 15 mg), and tetrahydrofuran (10 ml). The mixture was stirred and maintained under a hydrogen pressure of 50 psi for 8 hrs. At the end of reaction, the resulting suspension was centrifuged to remove catalyst residues. The solution was then dried by solvent evaporation to give yellow-brown solids of poly(aminohydroxy) fullerene (25 mg).

EXAMPLE 9

A reaction flask (50 ml) charged with a fullerene mixture of carbon 60 and carbon 70 (100 mg) was treated with concentrated nitric acid (10 ml) while vigorously stirring. The suspension was heated at 75° C. for 2 days. At the end of reaction, water (20 ml) was added to cause the precipitation of poly(nitrohydroxy) fullerene (110 mg). IR (KBr) $\upsilon_{max}$ 3410 (s, br), 1629, 1566 (s), 1341, 1084, and 816 cm$^{-1}$.

To a thick-wall reactor (25 ml) connected with a hydrogen cylinder was charged the poly(nitrohydroxy) fullerene (40 mg), palladium on carbon (Pd/C, 5 mg), and tetrahydrofuran (10 ml). The mixture was stirred and maintained under a hydrogen pressure of 50 psi for 6 hrs. At the end of reaction, the resulting suspension was filtered through celite to remove catalyst residues. The filtrate was then dried by solvent evaporation to give brown solids of poly(aminohydroxy) fullerene (33 mg).

EXAMPLE 10

A reaction flask (25 ml) charged with a fullerene mixture of carbon 60 and carbon 70 (70 mg) in methylene chloride (1 ml, dried over molecular sieve) was treated with nitronium tetrafluoroborate (0.5 m in sulfolane solution), NO$_2$BF$_4$ (100 mg) and acetonitrile (1.0 ml). The mixture was stirred at 23° C. for a period of 15 hrs. Water was added (0.5 ml) and the stirring continued for another 2 hrs. Organic solvents were evaporated under reduced pressure and more water was added to cause the precipitation of brown solids. The solid was collected by the centrifuge technique, washed with water, and dried in vacuum to obtain poly(nitroacetamino) fullerene (82 mg). IR (KBr) $\upsilon_{max}$ 1656, 1563, 1330, 1076, and 807 cm$^{-1}$.

To a thick-wall reactor (25 ml) connected with a hydrogen cylinder was charged the poly(nitroacetamino) fullerene (40 mg), palladium on carbon (Pd/C, 5 mg), and tetrahydrofuran (10 ml). The mixture was stirred and maintained under a hydrogen pressure of 50 psi for 6 hrs. At the end of reaction, the resulting suspension was filtered through celite to remove catalyst residues. The filtrate was then dried by solvent evaporation to give brown solids of poly(aminoacetamino) fullerene (28 mg).

To a reaction flask (25 ml) charged with the poly(aminoacetamino) fullerene (30 mg) and methanol (10 ml) sodium hydroxide (100 mg) was added. The mixture was heated at 60°-70° C. for overnight with stirring. At the end of reaction, water (50 ml) and NaOH (100 mg) were added to cause the precipitation of poly(amino) fullerene (19 mg).

EXAMPLE 11

A reaction flask (25 ml) charged with a fullerene mixture of carbon 60 and carbon 70 (200 mg), m-chloroperbenzoic acid (MCPBA, 800 mg), and chloroform (50 ml) was maintained under an atmospheric pressure of inert gas (N$_2$). The mixture was heated to 70° and stirred at that temperature for a period of 16 hrs. Another portion of chloroform (50 ml) was then added and centrifuged to isolate the chloroform-insoluble brown solids. After washing the solid with more chloroform, it was redissolved in acetone (40 ml), filtered through celite, and the solvent evaporated to afford poly(α-hydroxy m-chlorobenzocarboxy) fullerene (350 mg). Elemental analysis gives C, 65.81; H, 1.97; 0, 20.21; Cl, 8.56. IR (KBr) $\upsilon_{max}$ 3424 (s, broad), 1734 (carbonyl), 1626, 1286 (w), 1251, 1078 (broad), and 745 cm$^{-1}$. Mass spectrum yields: m/e 720, 765, 769, 793, 817, 841, 853, 857, 869, 889, 901, 919, 933, 941, 951, 977, 995, 1023, 1037, 1071, 1085, 1127, 1143, 1159, 1193, 1211, 1239, 1255, 1333, 1359, and 1381.

To a reaction flask (25 ml) charged with poly(α-hydroxy m-chlorobenzocarboxy) fullerene (100 mg) and methanol (10 ml) sodium hydroxide (150 mg) was added. The mixture was heated at 60°-70° C. for overnight with stirring. At the end of reaction, water (50 ml) and NaOH (200 mg) were added to cause the precipitation of polyhydroxylated fullerene (45 mg). (KBr) $\upsilon_{max}$ 3416 (s, broad), 1586, 1391, 1068, and 550 (w, broad) cm$^{-1}$.

EXAMPLE 12

In a typical reaction, a finely divided polyhydroxylated fullerene prepared in accordance with Example 1 (1 to 6% by weight of total acid chloride used) was suspended in pyridine (100 parts), which was dried over molecular sieve, and stirred at ambient temperature for 30 min. Sebacoyl chloride [ClCO(CH$_2$)$_8$COCl, 2 parts] was added slowly and the mixture was heated at 75° C. for a period of 16 hours. 1,6-hexanediol (5 parts) and sebacoyl chloride (3 parts) was then added slowly. The reaction was allowed to continue for an additional 16 hrs at 75° C. At the end of reaction, diethyl ether (500 parts) was added to cause the precipitation of polymer products. The precipitates were filtered, washed with diethyl ether and water, and dried to afford brown solids of polyester. The solid was further suspended and stirred in dilute HCl solution (1N) for 2 hrs to remove the unreacted polyhydroxylated fullerene from the polyester.

In a separated reaction, an equal molar quantity of sebacoyl chloride and 1,6-hexanediol were allowed to polymerize in pyridine under similar conditions as described above to give a control polyester. The comparison of physical properties between polyester (containing bonded polyhydroxylated fullerene) and polyester (containing no polyhydroxylated fullerene) was carried out by differential scanning calorimetry (DSC) and thermogravimetry analysis (TGA) measurements. As a result, we observed a significant improvement of thermal stability of the polyester containing the polyhydroxylated fullerene than that without at high temperatures above 200° C. with much less weight loss (50% for polyester containing 1.5% of polyhydroxylated fullerene and 27% for the polyester containing 3% of the polyhydroxylated fullerene as compared to 64% for the polyester without the polyhydroxylated fullerene at 360° C.) as shown in their TGA data. The comparison between DSC data taken for the polyesters indicated a shift of $T_g$ in the polyester containing polyhydroxylated fullerene (below ambient temperature) from 130° C. for the polyester without polyhydroxylated fullerene.

What is claimed is:

1. A process of forming polysubstituted fullerene comprising contacting a fullerene with an electrophilic reagent selected from the group consisting of nitronium ion and organic peracid, provided that when said electrophilic reagent is nitronium ion, the contacting is for a time and at a temperature sufficient to form a carbocation of the fullerene and said carbocation of the fullerene is thereafter contacted with a nucleophilic reagent selected from the group consisting of water and organic acids having the general formula

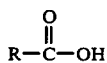

where R is a substituted or nonsubstituted alkyl or aryl group and wherein the substituent group is selected from —OR'; halides; —NO$_2$; —CN; and —NHCOR', and wherein R' is an aliphatic group; and when the electrophilic reagent is an organic peracid, the contacting is for a time and at a temperature sufficient to form a poly(hydroxyorganocarboxy) fullerene.

2. The process according to claim 1 wherein the electrophilic reagent is nitronium ion and said nitronium ion is generated in situ, said temperature is between about 90° and about 115° C., and wherein when said nitronium ion is available directly, said temperature is about 20° to about 50° C.

3. The process of claim 1 wherein when the electrophilic reagent is an organic peracid, whereby a poly(hydroxyorganocarboxy) fullerene is formed, said poly(hydroxyorganocarboxy) fullerene is further hydrolyzed to form a polyhydroxylated fullerene.

4. The process according to claim 1 whereby a poly(nitrohydroxy) fullerene having both hydroxy and nitro groups on said poly(nitrohydroxy) fullerene is formed, further comprising hydrogenating said nitro groups to form a poly(aminohydroxy) fullerene.

* * * * *